APPLE TREE
Filed Feb. 28, 1972 2 Sheets-Sheet 1
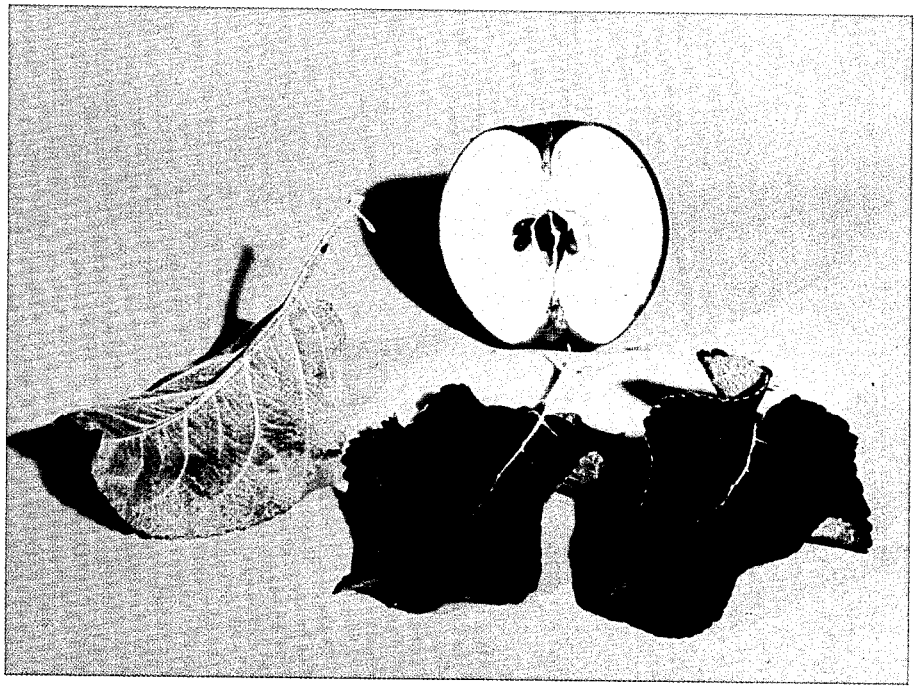
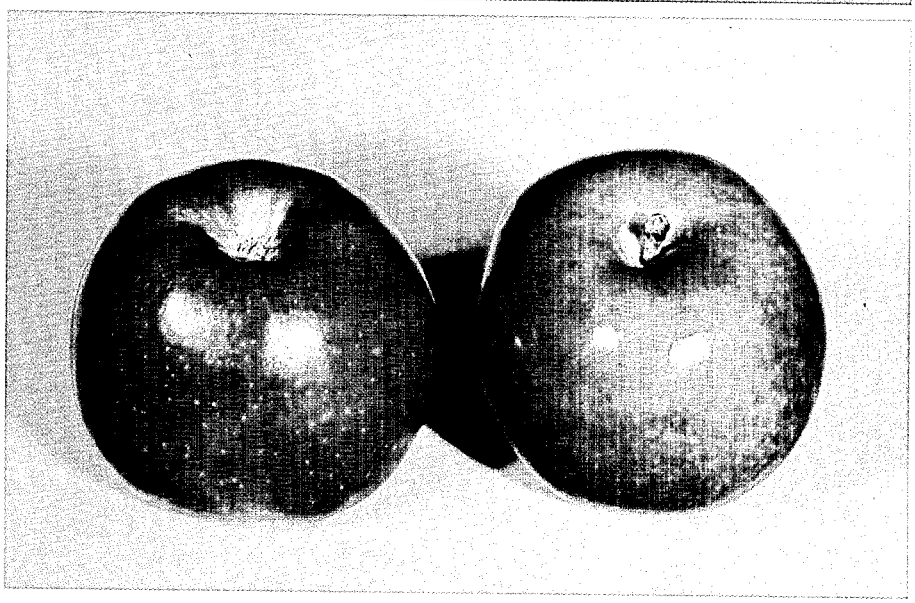

APPLE TREE
Filed Feb. 28, 1972 2 Sheets-Sheet 2
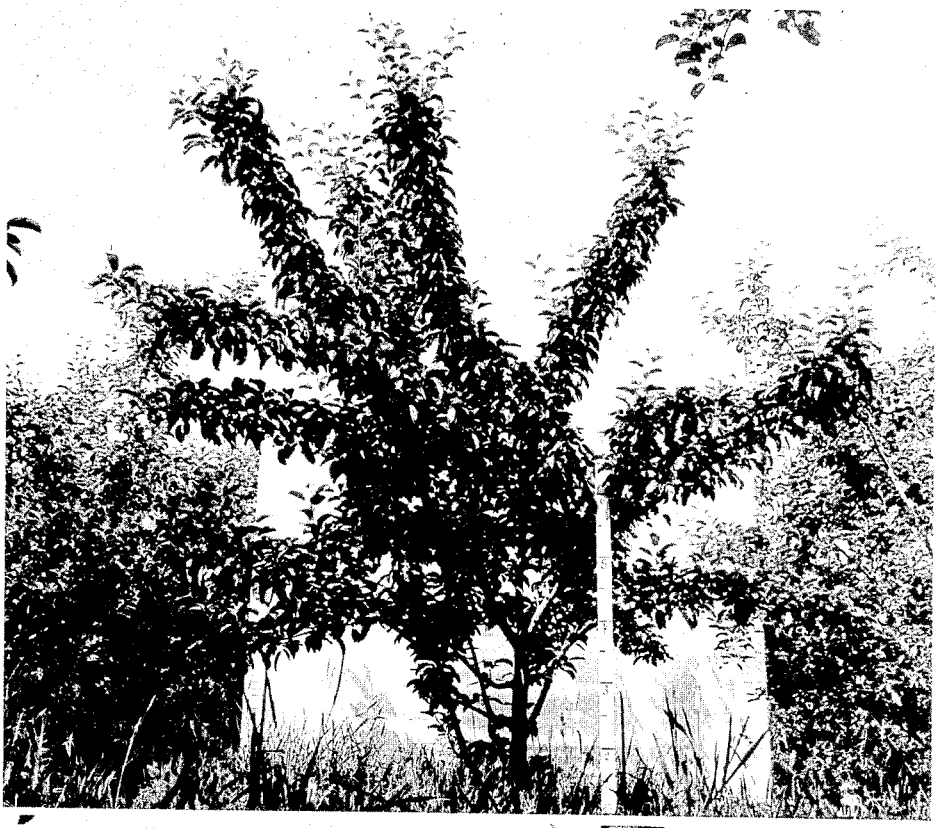
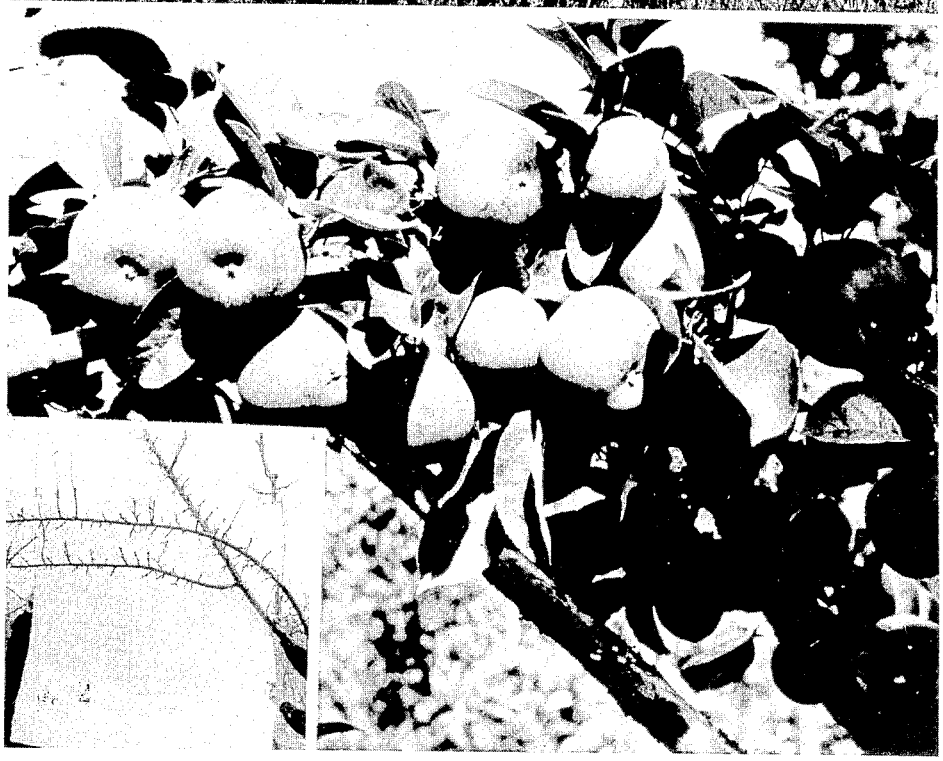

United States Patent Office

Plant Pat. 3,390
Patented Aug. 21, 1973

3,390
APPLE TREE

Walter E. Raikes, Okanogan Mission, British Columbia, Canada, assignor to Columbia & Okanogan Nursery Co., Inc., Wenatchee, Wash.

Filed Feb. 28, 1972, Ser. No. 230,166
Int. Cl. A01h 5/03
U.S. Cl. Plt.—34 1 Claim The present invention relates to a new and distinct variety of apple tree which was discovered by me as a whole tree sport on my cultivated orchard property located at Okanogan Mission, in the province of British Columbia, Canada.

At the time of my discovery aforesaid, I was growing in my orchard a block of apple trees of the unpatented variety known as "Red McIntosh" (Summerland Strain). In the course of my development and care of these trees, my attention was drawn to one particular tree because of its unusual habits of growth which materially differed from the normal habits of all other trees in the block, as well as from the trees of the many other apple varieties familiar to me. I thereupon took steps to carefully preserve this sport tree and to keep it under close and continued observation. In due course, I also took steps to have it asexually reproduced on my behalf, both in Canada and in the United States at the Washington State Experiment Station located at Moxee, Wash. After extensive observations and tests of the original tree and its progeny derived therefrom by both budding and grafting, I am convinced that my new sport is definitely distinguished from its parent variety and from all other varieties including other sports of the parent variety, as evidenced by the following unique combination of characteristics which are outstanding in my new sport and which are established and come true through succeeding asexual propagations performed by both budding and grafting:

(1) An upright or columnar and exceptionally open habit of tree growth, with limited main limb development confined to a few limbs which have a very limited, if any, side shoot development, while providing an exceptionally strong tree framework capable of sustaining heavy loads of fruit without bending, splitting, breaking or other damage attributable to the heavy weight of fruit borne thereby;

(2) A somewhat drooping leaf habit, with the leaves being somewhat larger in size, more abundant in number and deeper green in color (near Ivy green) than those of the parent variety;

(3) A spur type fruiting habit, with the spurs being more numerous per unit length of wood and more extensively distributed throughout the tree than in any other known spur type apple tree variety;

(4) A remarkably large fruit size in relation to heaviness of fruit crop to an exceptional degree not found in other spur type apple varieties, with the fruit being borne closer together and virtually completely covering each limb along substantially the full length thereof;

(5) A good blushed solid bright red fruit color (Amaranth Red) generally comparable to the fruit of the parent variety "Red McIntosh" (Summerland Strain);

(6) Extremely good productivity evidenced by heavy fruit crops consistently produced annually even when "Red McIntosh" and other sports thereof bear poorly or almost no fruit at all on occasion in the same orchard; and (7) Superior frost resistance of the fruit buds.

The most striking feature of my new sport is the appearance of the tree which is much more open but stronger than the tree form of Summerland "Red McIntosh," as well as that of another sport thereof known as "Mac Spur" (U.S. Plant Pat. No. 2,982). In addition, the fruit spurs are even more numerous and closer together than in either of the latter varieties or in other known strains of the spur type. These features of my new sport combined with its exceptionally larger fruit size and more consistently heavy annual bearing habit, have been recognized by testing stations and experts in both Canada and the United States as constituting a new and distinct and commercially valuable variety.

The accompanying drawings show typical specimens of the foliage and fruit of my new variety as depicted in color, as well as a typical specimen whole tree and portions of specimen limbs in both fruit-bearing and dormant stages as depicted in black and white, with the dormant limbs more clearly showing the extensive and closely spaced spur habit.

The following is a detailed description of my new variety, with color terminology in accordance with Koster's Color Guide, except where general color terms of ordinary dictionary significance are obvious:

Locality where grown and observed: Okanogan Mission, B.C., Canada.

Dates of first and last pickings: About September 27 and about September 30, respectively, or earlier, depending on seasonal conditions.

Tree: Large; medium vigorous; upright or columnar; very open as the result of limited main limb development and limited, if any, lateral shoot development; slow growing; hardy; very productive; regular bearer.

*Trunk.*—Stocky; shaggy.

*Branches.*—Thick; very strong; shaggy; little-branched. Color—Brown.

*Lenticels.*—Medium number; medium size.

Foliage:

*Leaves.*—Large; long (from about 3½ inches to 5 inches); wide (from about 2½ inches to about 3½ inches); ovate; taper-pointed; thick; rugose. Color—Ivy green, Color No. 83. Margin—glandular; coarsely serrate. Petiole—from short to medium length (from about 1 inch to 1½ inches); thick.

Flowers: Similar to "Red McIntosh" Summerland Strain.

*Dates of first and full bloom.*—Same as Summerland "Red McIntosh."

*Size.*—Large.

*Color.*—Pink.

Fruit: Similar to Summerland "Red McIntosh."

*Maturity when described.*—Eating ripe about September 25 depending on season.

*Size.*—Uniform. Axial diameter—from about 3 inches to 3¼ inches. Transverse diameter—from about 2¾ inches to 3 inches.

*Form.*—Uniform; compressed laterally; truncate at base; ovoid.

*Cavity.*—Symmetrical; from acute to acuminate. Depth—From about ¼ inch to ⅜ inch. Breadth—From about ¾ inch to 1 inch.

*Basin.*—Symmetrical; abrupt; wide base.

*Stem.*—Medium stout. Length—about ½ inch.

*Calyx.*—Closed; segments persistent; narrowly acuminate; from about ¾ inch to 1 inch long; prostrate; outer surface glaborous; inner surface pubescent.

*Eye.*—Small; partially closed.

*Skin.*—Thin; tender; smooth; glossy; waxed. Dots—Obscure; many; small; circular. Color—whitish. Distribution—uniform. Ground color—pale yellow. Color markings—blushed; self-colored; bright. Color—Solid Red, near Amaranth Red, Color No. 43. General color effect—solid bright red. Bloom—abundant; evenly distributed.

*Flesh.*—Juicy. Color—white, with yellowish tint. Texture—firm; tender; fine; crisp. Flavor—subacid; sprightly. Aroma—distant. Quality—very good.

*Core.*—Median. Bundle area—Medium size; oblate; symmetrical. Halves of core—equal. Bundles—conspicuous. Color—yellowish. Alternate bundle—reaches tube below stamens. Core lines—distinct in cross section. Carpellary area—Distinct; large. Calyx tube—glabrous toward base; funnel form. Stem of funnel—short. Depth of tube to shoulder—about ½ inch. Entire depth—about ¾ inch. Styles—present; united; glabrous. Stamens—obscure; median. Auxiliary cavity—wanting. Seed cells—abaxile; open. Cell walls—thin; tender. Length—about ¾ inch. Breadth—about ⅜ inch. Longitudinal section—oval; obtuse at apex. Surface—smooth; tufted. Cross section—broad.

Seeds: 10 perfect; 2 imperfect; not more than 3 in one cell.

Length.—About ⅜ inch.

Breadth.—About 9/16 inch.

Form.—Acute.

Color.—Medium brown, near Van Dyck Brown, Color No. 96.

Use: Market; dessert; culinary.

Keeping quality: Good; 3 months or more in ordinary storage.

Disease and insect resistance: Good; not as subject to mildew as some varieties when grown under the same conditions in the same region.

I claim:

1. A new and distinct variety of apple tree, substantially as herein shown and described, characterized particularly as to novelty by the unique combination of an upright or columnar and exceptionally open habit of tree growth, with limited main limb development confined to a few limbs which have a very limited, if any, side shoot development, while providing an exceptionally strong tree framework capable of sustaining heavy loads of fruit without bending, splitting, breaking or other damage attributable to the heavy weight of fruit borne thereby, a somewhat drooping leaf habit, with the leaves being somewhat larger in size, more abundant in number and deeper green in color (near Ivy Green) than those of the parent variety, a spur type fruiting habit, with the spurs being more numerous per unit length of wood and more extensively distributed throughout the tree than in any other known spur type apple tree variety, a remarkably large fruit size in relation to heaviness of fruit crop to an exceptional degree not found in other spur type apple varieties, with the fruit being borne closer together and virtually completely covering each limb along substantially the full length thereof, a good blushed solid bright red fruit color (Amaranth Red) generally comparable to the fruit of the parent variety, "Red McIntosh" (Summerland Strain), extremely good productivity evidenced by heavy fruit crops consistently produced annually even when "Red McIntosh" and other sports thereof bear poorly or almost no fruit at all on occasion in the same orchard, and superior frost resistance of the fruit buds.

No references cited.

ROBERT E. BAGWILL, Primary Examiner